United States Patent [19]

Yoshioka et al.

[11] Patent Number: 4,939,248

[45] Date of Patent: Jul. 3, 1990

[54] OPTICALLY ACTIVE AZETIDINONES

[75] Inventors: Takeo Yoshioka, Ayase; Machiko Watanabe, Fujisawa; Yasuo Fukagawa, Kamakura; Tomoyuki Ishikura, Chigasaki, all of Japan

[73] Assignee: Sanraku Incorporated, Tokyo, Japan

[21] Appl. No.: 246,826

[22] PCT Filed: Dec. 18, 1987

[86] PCT No.: PCT/JP87/00991

§ 371 Date: Aug. 18, 1988

§ 102(e) Date: Aug. 18, 1988

[87] PCT Pub. No.: WO88/04656

PCT Pub. Date: Jun. 30, 1988

[30] Foreign Application Priority Data

Dec. 22, 1986 [JP] Japan ................................. 61-303915

[51] Int. Cl.$^5$ ............................................. C07D 405/04
[52] U.S. Cl. ......................................................... 540/200
[58] Field of Search .......................................... 540/200

[56] References Cited

FOREIGN PATENT DOCUMENTS 146735 7/1985 European Pat. Off. ............ 540/200

OTHER PUBLICATIONS

Matsunoga et al., "Tetrahedron Letters", vol. 24, No. 29, pp. 3009-3012 (1983).

Primary Examiner—Mary C. Lee
Assistant Examiner—Robert C. Whittenbaugh
Attorney, Agent, or Firm—Wenderoth, Lind & Ponack

[57] ABSTRACT

This invention provides compounds of the formula

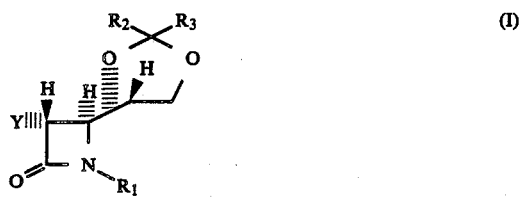

wherein Y represents an acetyl, 1-hydroxyethyl or 1-fluoroethyl group, $R_1$ represents a hydrogen atom or an easily splittable amino-protecting group, and $R_2$ and $R_3$ are identical or different and each represents a hydrogen atom, a lower alkyl group, a phenyl group, a benzyl group or a diphenylmethyl group, or $R_2$ and $R_3$ together represent a lower alkylene group; and processes for production thereof. These compounds are useful as synthesis intermediates for production of various medicines, particulary carbapenam or carbapenem antibiotics, such as a carbapenem antibiotic of the following formula which has excellent antimicrobial activity and relatively good stability to kidney dehydropeptidase.

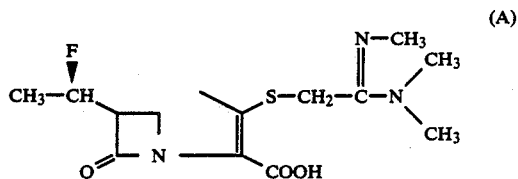

10 Claims, No Drawings

OPTICALLY ACTIVE AZETIDINONES

DESCRIPTION

1. Technical Field

This invention relates to novel 3-substituted azetidinone compounds, and more specifically, to compounds represented by the following formula

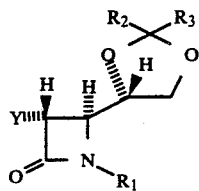

wherein Y represents an acetyl, 1-hydroxyethyl or 1-fluoroethyl group, $R_1$ represents a hydrogen atom or an easily splittable amino-protecting group, and $R_2$ and $R_3$ are identical or different and each represents a hydrogen atom, a lower alkyl group, a phenyl group, a benzyl group or a diphenylmethyl group, or $R_2$ and $R_3$ together represent a lower alkylene group.

2. Background Art

3-Substituted azetidinone derivatives, particularly 3-substituted azetidinone derivatives having an S-configuration at the 4-position, are useful as intermediates for the production of various antimicrobial beta-lactam compounds such as carbapenem and carbapenem antibiotics, and various types of azetidinone derivatives have been previously proposed.

DISCLOSURE OF THE INVENTION

The present inventors have now found that 3-substituted azetidinone derivatives having an S-configuration at the 4-position represented by the above formula (I) can be stereo selectively obtained by using relatively inexpensive D-mannitol as a starting material, and reacting a ketal compound of D-glyceraldehyde derived from the starting material with diketene in the presence of a certain azole compound. This discovery has led to the accomplishment of the present invention.

The compounds of formula (I) provided by this invention are useful as synthesis intermediates for various medicines, particularly carbapenem or carbapenem antibiotics, for example an antibiotic of the following formula which is known to have excellent antimicrobial activity and relatively good stability to kidney dehydropeptidase.

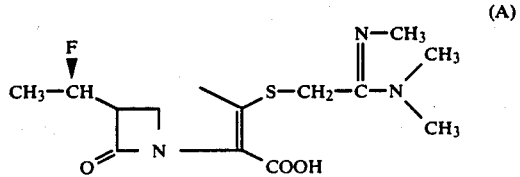

(A)

The term "lower", as used in this specification to qualify a group or a compound, means that the group or compound so qualified has not more than 8 carbon atoms, preferably not more than 6 carbon atoms.

The "easily splittable amino-protecting group" includes amino-protecting groups that can be eliminated from compounds, to which they are bonded, by hydrolysis, reduction, oxidation, or otherwise without substantially affecting the other functions of the compounds adversely. Examples are tri(lower alkyl)silyl groups such as trimethylsilyl and tert-butyldimethylsilyl; a benzyl group which may be substituted by one or two lower alkoxy groups, such as benzyl, methoxybenzyl and dimethoxybenzyl; and a phenyl group which may be substituted by one or two lower alkoxy groups, such as methoxyphenyl and dimethoxyphenyl.

The "lower alkyl group" may be linear or branched, and includes, for example, methyl, ethyl, n-propyl, isopropyl, n-butyl, sec-butyl, isobutyl and tert-butyl.

The "lower alkylene group" preferably has 4 to 5 carbon atoms as in tetramethylene and pentamethylene.

The hydroxyl group and the fluorine atom in 1-hydroxyethyl and 1-fluoroethyl groups represented by Y in formula (I) may take either an S- or an R-configuration. In general, the fluorine atom desirably takes an R-configuration.

Typical examples of the compounds of formula (I) provided by this invention include
3S,4S)-3-acetyl-4-[(4S)-2,2-dimethyl-1,3-dioxolan-3-yl]-1-(4-methoxy)phenyl-2-azetidinone,
(3S,4S)-4-[(4S)-2,2-dimethyl-1,3-dioxolan-4-yl]-3-[(1S)-1-hydroxyethyl]-1-(4-methoxy)phenyl-2-azetidinone,
(3S,4S)-4-[(4S)-2,2-dimethyl-1,3-dioxolan-4-yl]-3-[(1R)-1-hydroxyethyl-1-(4-methoxy)phenyl-2-azetidinone,
(3R,4S)-4-[(4S)-2,2-dimethyl-1,3-dioxolan-4-yl]-3-[(1R)-1-fluoroethyl]-1-(4-methoxy)phenyl-2-azetidinone,
(3S,4S)-3-acetyl-1-benzyl-4-[(4S)-2,2-dimethyl-1,3-dioxolan-4-yl]-2-azetidinone,
(3S,4S)-1-benzyl-4-[(4S)-2,2-dimethyl-1,3-dioxolan-4-yl]-3-(1S)-hydroxyethyl]-2-azetidinone,
(3S,4S)-1-benzyl-4-[(4S)-2,2-dimethyl-1,3-dioxolan-4-yl]-3-[(1R)-1-hydroxyethyl]-2-azetidinone,
(3R,4S)-1-benzyl-4-[(4S)-2,2-dimethyl-1,3-dioxolan-4-yl]-2-[(1R)-1-fluoroethyl]-2-azetidinone,
(3S,4S)-3-acetyl-1-(2,4-dimethoxy)phenyl-4-[(4S)-2,2-dimethyl-1,3-dioxolan-4-yl]-2-azetidinone,
(3S,4S)-1-(2,4-dimethoxy)phenyl-4-[(4S)-1,3-dioxolan-4-yl]-3-[(1S)-1-hydroxyethyl]-2-azetidinone,
(3S,4S)-1-(2,4-dimethoxy)phenyl-3-[(1R)-1-hydroxyethyl]-4-[(4S)-2-phenyl-1,3-dioxolan-4-yl]-2-azetidinone,
(3R,4S)-1-(2,4-dimethoxy)phenyl-4-{(2S)-1,4-dioxospiro[4,5]deca-2-yl}-3-[(1R)-1-fluoroethyl]-2-azetidinone,
(3S,4S)-3-acetyl-1-(4-methoxy)benzyl-4-[(4S)-2,2-dimethyl-1,3-dioxolan-4-yl]-2-azetidinone,
(3S,4S)-3-[(1S)-1-hydroxyethyl]-1-(4-methoxy)benzyl-4-[(4S)-2-phenyl-1,3-dioxolan-4-yl]-2-azetidinone,
(3S,4S)-4-[(4S)-1,3-dioxolan-4-yl]-3-[(1R)-1-hydroxyethyl]-1-(4-methoxy)benzyl-2-azetidinone,
(3R,4S)-4-[(4S)-2-ethyl-2-methyl-1,3-dioxolan-4-yl]-3-[(1R)-1-fluoroethyl]-1-(4-methoxy)benzyl-2-azetidinone,
(3S,4S)-3-acetyl-4-[(4S)-2,2-dimethyl-1,3-dioxolan-4-yl]-1-trimethylsilyl-2-azetidinone,
(3S,4S)-1-t-butyldimethylsilyl-4-[(4S)-2,2-diphenyl-1,3-oxolan-4-yl]-3-[(1S)-hydroxyethyl]-2-azetidinone,
(3S,4S)-4-[(4S)-2,2-dimethyl-1,3-dioxolan-4-yl]-3-[(1R)-1-hydroxyethyl]-1-trimethylsilyl-2-azetidinone,
(3R,4S)-1-t-butyldimethylsilyl-3-[(1R)-1-fluoroethyl]-4-[(4S)-2-methyl-1,3-dioxolan-4-yl-2-azetidinone,
(3S,4S)-3-acetyl-1-(2,4-dimethoxy)benzyl-4-[(4S)-2-phenyl-1,3-dioxolan-4-yl]-2-azetidinone,
(3S,4S)-3-acetyl-4-[(4S)-2,2-diphenyl-1,3-dioxolan-4-yl]-1-(4-methoxy)phenyl-2-azetidinone, and (3S,4S)-3-acetyl-4-[(4S)-1,3-dioxolan-4-yl]-(4-methoxy)-phenyl-2-azetidinone.

A compound of formula (I) in which Y represents an acetyl group can be produced, for example, by reacting a compound represented by the following formula

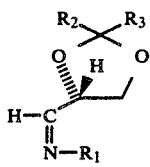

(II)

wherein $R_1$, $R_2$ and $R_3$ are as defined hereinabove, with diketene of the following formula

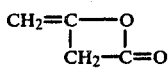

(IV)

in the presence of an azole compound represented by the following formula

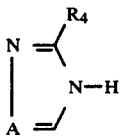

(III)

wherein A represents

$$\begin{array}{c} R_5 \\ | \\ CH \end{array}$$

or N, and $R_4$ and $R_5$ are identical or different and each represents a hydrogen atom or a lower alkyl group.

The reaction of the compound of formula (II) with the diketene of formula (IV) may be carried out at a temperature of generally from about $-40°$ C. to about $40°$ C., preferably from about $-20°$ C. to about $25°$ C. in the presence or absence of a suitable solvent. Examples of the solvent are halogenated hydrocarbons such as methylene chloride, chloroform and dichloroethane, ester-type hydrocarbons such as ethyl acetate and butyl acetate, ether-type hydrocarbons such as diethyl ether, tetrahydrofuran and dioxane, and dimethylformamide.

The proportion of the compound of formula (II) relative to the diketen of formula (IV) is not strictly limited, and may be varied widely depending, for example, upon the type of the compound of formula (II) and the reaction temperature. Generally, it is convenient to use 0.5 to 3 moles, preferably 0.8 to 1.5 moles, of the compound of formula (II) per mole of the diketene of formula (IV).

Examples of the azole of formula (III) used in the above reaction include imidazole, 2-methylimidazole, 4-methylimidazole, 2,4-dimethylimidazole, 1,2,4-triazole, 3-methyl-1,2,4-triazole, 5-methyl-1,2,4-triazole, and 3,5-dimethyl-1,2,4-triazole. The suitable proportion of the azole used is generally 0.5 to 3 moles, preferably 1 to 1.5 moles, per mole of the compound of formula (II). When a triazole is used, an organic base such as triethylamine, tributylamine, diethylisopropylamine or 1,8-diazabicyclo[5.4.0]-7-undecene should be used as a reaction aid.

The above reaction yields the compound of formula (I) in which Y is an acetyl group. This compound can be easily isolated and purified from the reaction mixture by methods known per se, such as extraction with organic solvent, crystallization or silica gel column chromatography.

As an alternative, the compound of formula (I) in which Y is an acetyl group may be produced by reacting the compound of formula (II) with the azole compound of formula (III), and reacting the resulting compound of the following formula

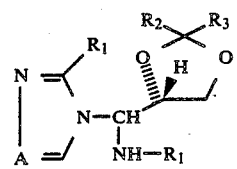

(V)

wherein A, $R_1$, $R_2$, $R_3$ and $R_4$ are as defined hereinabove, with the diketene of formula (IV).

The reaction of the compound of formula (V) with the diketene of formula (IV) may be carried out usually in a solvent of the type mentioned above at a temperature of generally from about $-30°$ C. to about $40°$ C., preferably from about $-20°$ C. to about $25°$ C.

The proportion of the compound of formula (V) with respect to the diketene of formula (IV) is not strictly limited, and may be varied according to the type of the compound of formula (V) and the reaction temperature, for example. Generally, the compound of formula (V) is used preferably in a proportion of 0.5 to 2 moles, especially 0.8 to 1 mole, per mole of the diketene of formula (IV).

The resulting compound of formula (I) in which Y is an acetyl group can be isolated and purified from the reaction mixture by the same means as above.

The compound of formula (II) used as a starting material in the above reactions is known per se, and can be easily produced, for example, by oxidative cleavage of 1.2,5.6-di-O-ketalized D-mannitol represented by the following formula

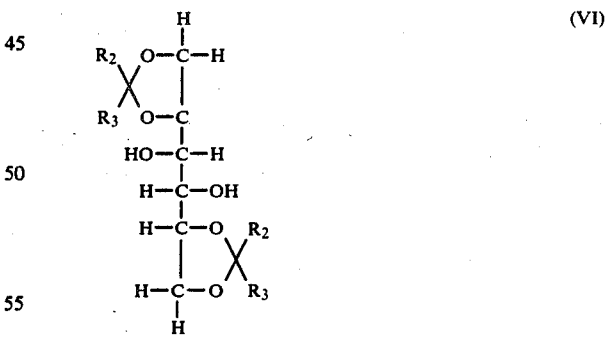

(VI)

wherein $R_2$ and $R_3$ are as defined, (by using periodic acid or lead tetraacetate, for example) to form a ketal compound of D-glyceraldehyde represented by the following formula

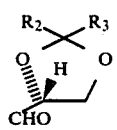

(VII)

wherein R$_2$ and R$_3$ are as defined above, and reacting the resulting ketal compound with an amine represented by the following formula $$R_1-NH_2 \quad (VIII)$$

wherein R$_1$ is as defined above, to form a Schiff base.

The compound of formula (V), on the other hand, is a novel compound not described in the prior literature, and can be produced, for example, by reacting the compound of formula (II) with the azole compound of formula (III) in a solvent of the type mentioned above with regard to the reaction of the compound of formula (II) with the diketene of formula (IV). The suitable reaction temperature is generally from about −40° C. to about 40° C., preferably from about −20° C. to about 25° C. The proportion of the compound of formula (III) with regard to the compound of formula (II) is not strictly limited. Generally, however, it is convenient to use the compound of formula (III) in a proportion of 0.5 to 2 moles, preferably 1 to 1.5 moles, per mole of the compound of formula (II).

The resulting compound of formula (V) may be isolated from the reaction mixture and then reacted with the ketene of formula (III). If desired, the reaction mixture may be directly submitted to the reaction with the diketene of formula (II) without isolating the compound of formula (V).

When the compound of formula (I) in which Y is an acetyl group is subjected to reduction, the acetyl group can be converted to a 1-hydroxyethyl group. Reduction of the compound of formula (I) in which Y is an acetyl group may usually be carried out in a solvent, for example, ether-type hydrocarbons such as diethyl ether, tetrahydrofuran and dimethoxyethane, alcohol-type hydrocarbons such as ethanol and methanol, and aromatic hydrocarbons such as benzene and toluene using a reducing agent such as sodium borohydride, lithium borohydride, lithium aluminum hydride, magnesium trifluoroacetate/diisopropylamine/borane, lithium tri-sec-butylborohydride (L-selectride ®, a registered trademark for lithium metal produced by Aldrich Chemical Corporation), potassium tri-sec-butylborohydride (K-selectride) and diisobutylaluminum hydride (DIBAL). By the suitable selection of the reducing agent, the 1-hydroxyethyl group can take different configurations. For example, when lithium borohydride or L-selectride ® is used, the 1S-hydroxyethyl group is obtained, and when diisobutyl aluminum hydride (DIBAL) or magnesium trifluoroacetate/diisopropylamine/borane is used, the 1R-hydroxyethyl group is obtained.

The above reduction may be carried out at a temperature of generally −78° C. to 40° C., preferably −78° C. to 25° C. The amount of the reducing agent is not critical. Generally, it is conveniently used in a proportion of 0.5 to 10 moles, preferably 1 to 4 moles, per mole of the compound of formula (I) in which Y is an acetyl group.

The resulting compound of formula (I) in which Y is a 1-hydroxyethyl group may be fluorinated to give a compound of formula (I) in which Y represents a 1-fluoroethyl group. Fluorination of the compound of formula (I) in which Y is a 1-hydroxyethyl group may be carried out by methods known per se, for example, by the method described by Ching-Pong Mak et al. (Heterocycles, 19, 1399 (1982)), or by using Ishikawa reagent (a mixture of hexafluoropropene and diethylamine). As a result, OH of the S-configuration in the 1-hydroxyethyl group is stereo selectively substituted by F of the R-configuration, and the corresponding compound of formula (I) in which Y is a 1R-fluoroethyl group can be obtained.

The compound of the following formula thus obtained:

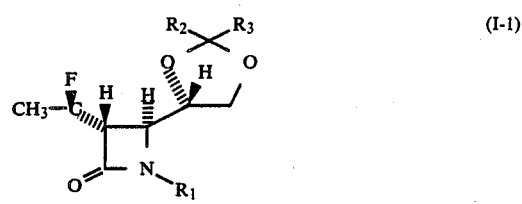

wherein R$_1$, R$_2$ and R$_3$ are as defined hereinabove, may be converted to the above-listed antibiotic of formula (A) in accordance with the following reaction scheme A:

Reaction scheme A

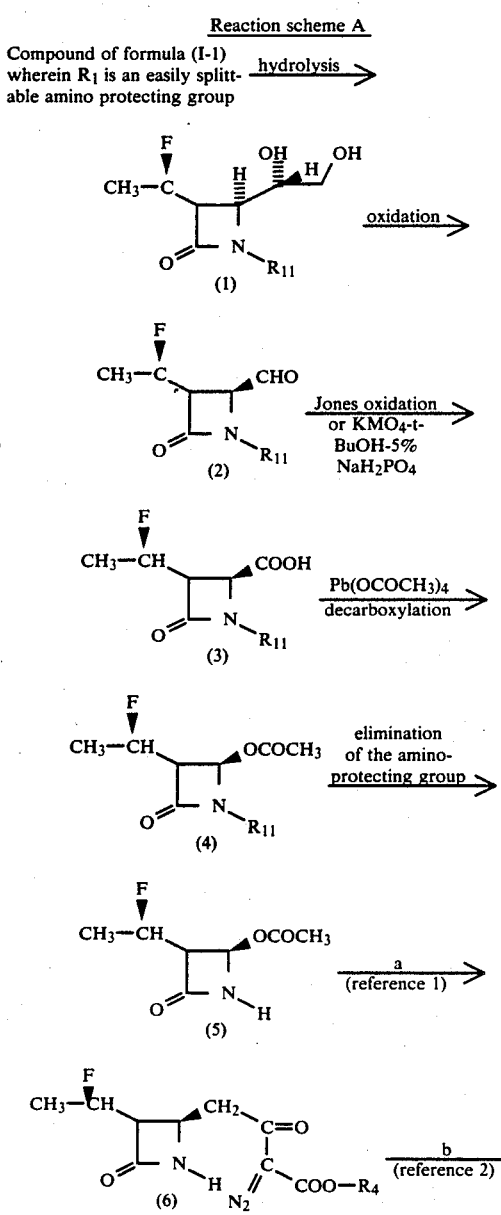

-continued
Reaction scheme A

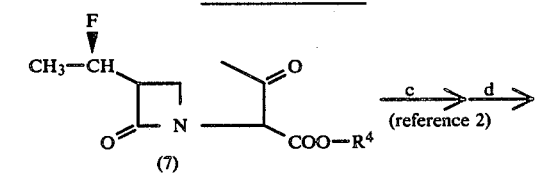
(7)

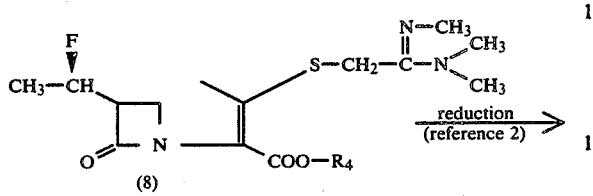
(8)

compound of formula (A)

In the above reaction scheme, $R_{11}$ represents an easily splittable amino-protecting group.

Hydrolysis of the compound of formula (I-1) in which $R_1$ is an easily splittable amino-protecting group may be carried out in a manner known per se by treating the above compound with, for example, a mixture of acetic acid and water at a temperature of about 25° C. to about 60° C.

Usually, oxidation of the compound of formula (I) can be performed by using an oxidizing agent such as periodic acid, sodium meta-periodate or lead tetraacetate in a solvent such as benzene, toluene, tetrahydrofuran, tetrahyrofuran/water, dimethoxyethane/water, aqueous methanol, or aqueous ethanol. The above oxidation may be carried out at a temperature of generally from about −10° C. to about 50° C., preferably from about 0° C. to about 25° C.

The amount of the oxidizing agent to be used is not strictly restricted, and can be varied according to the type of the oxidizing agent. It is convenient to use the oxidizing agent in a proportion of generally 0.5 to 5 moles, preferably 1 to 1.5 moles, per mole of the compound of formula (1).

This hydrolysis gives the compound of formula (2) which can then be converted to the compound of formula (3) by subjecting to Jones oxidation or to oxidation with a reagent composed of $KMnO_4$/t-BuOH/5% $NaH_2PO_4$. The Jones oxidation or the oxidation with the above reagent may be carried out by the methods described by D. J. Hart et al. (Tetrahedron Letters, 26, 5493 (1985)) and Atsushi Abiko et al. (Tetrahedron Letters, 27, 4537 (1980)), for example.

The compound of formula (3) so obtained can then be converted into the compound of formula (4) by oxidative decarboxylation using lead tetraacetate. This oxidative decarboxylation may be carried out by methods known per se, for example, the method described by P. J. Reider et al. (Tetrahedron Letters, 23, 2293 (1982)). The compound (4) may be converted to the compound of formula (5) by eliminating the amino-protecting group at the 1-position using suitable deprotection methods depending upon the type of the amino-protecting group [for example, acid hydrolysis in the case of $R_{11}$ being a tri(lower alkyl)silyl group; hydrogenolysis in the case of $R_{11}$ being an unsubstituted or substituted benzyl group, and oxidative elimination in the case of $R_{11}$ being a p-methoxyphenyl or o,p-dimethoxyhenyl group]. If the amino-protecting group is a trimethylsilyl group, the compound (4) may be directly submitted to the subsequent reaction without deprotection.

The route from the compound (5) to the compound of formula (A) may be carried out in accordance with the methods described in the following references using the following reagents:

REAGENTS (a) $H_2C=C[OSi(CH_3)_3]-C(N_2)-COO-R_4$, $ZnI_2$
(b) $Rh_2(OCOCH_3)_4$
(c)

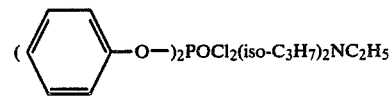

(d)

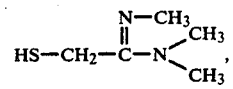

$(iso-C_3H_7)_2NC_2H_5$

REFERENCES (1) W. Flitsch et al., Tetrahedron Letters, 23, 2297 (1982)
(2) D. G. Melillo et al., Tetrahedron Letters, 21, 2783 (1980)

The antibiotic of formula (A) so produced is very useful as an antimicrobial agent, since it has a broad spectrum of excellent antimicrobial activity and is stable to kidney dehydropeptidase.

BEST MODE OF CARRYING OUT THE INVENTION

Referential Example

Production of N-(4-methoxy)phenyl-{[(4S)-2,2-dimethyl-1,3-dioxolan-4-yl]methane}imine:

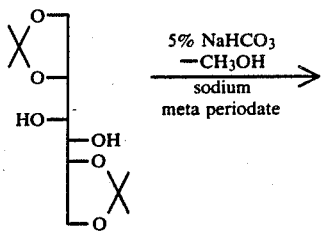

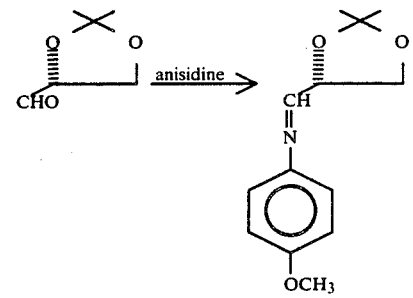

In 24 ml of methanol was dissolved 5 g (18 millimoles) of 1.2,5.6-di-O-isopropylidene-D-mannitol. Under ice cooling, a mixture of 7.75 ml of 5% sodium hydrogen carbonate, 5.865 g of meta periodic acid and 32.8 ml of water was added to the solution. At the above temperature, the mixture was stirred for 1 hour. The insoluble materials in the reaction solution were removed by filtration. The filtrate was extracted three times with methylene chloride. The extracts were combined, washed with a saturated aqueous solution of sodium chloride, and dried over anhydrous sodium sulfate. After drying, the sodium sulfate was removed by filtration, and the filtrate was concentrated to give 1,2-O-isopropylidene-D-glyceraldehyde by evaporating the methylene chloride alone under reduced pressure at a temperature below 20° C. Four fifths of the product of anisidine was dissolved in benzene, and in an atmosphere of nitrogen, added to a benzene solution of 1,2-O-isopropylidene-D-glyceraldehyde. An appropriate amount of anhydrous sodium sulfate was further added, and the mixture was stirred overnight. After the reaction, the sodium sulfate was removed by filtration, and the filtrate was concentrated to give 7.2 g (yield 80%) of the captioned compound.

$^1$H-NMR (CDCl$_3$; ppm):

1.45(s, 3H, 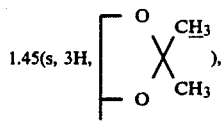

1.48(s, 3H, 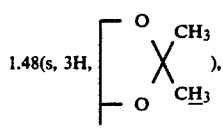

3.75(s, 3H, OC$\underline{H}$$_3$), 3.85–4.33(m, 2H, 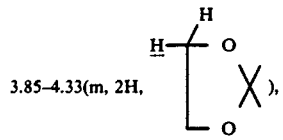

4.70(m, 1H, 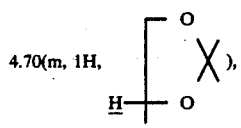

6.8(2H, d, J=8.5Hz 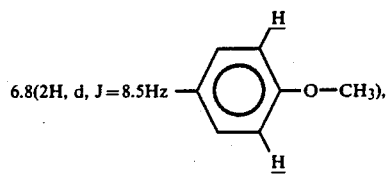

7.10(2H, d, J=8.5Hz 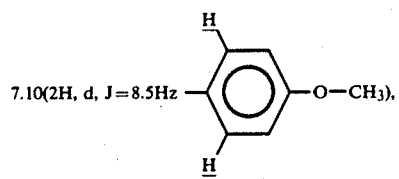

7.78(1H, d, J=5Hz —C=N—).
$\underline{H}$

IR$\nu_{max}^{CHCl_3}$(cm$^{-1}$)=1645 (—C=N), 1600.

EXAMPLE 1

Production of 1-{[(4S)-2,2-dimethyl-1,3-dioxolan-4-yl]-(4-methoxy)-phenylimino)methylimidazole

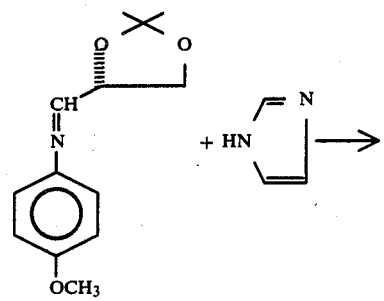

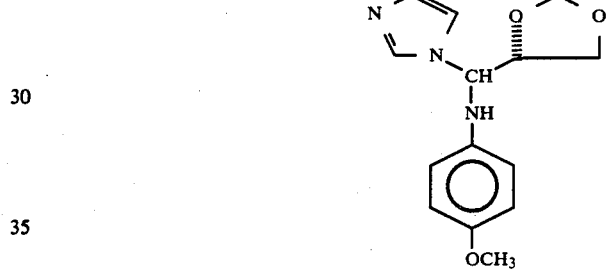

Thirty milligrams (0.13 millimole) of N-(4-methoxy)-phenyl-{[(4S)-2,2-dimethyl-1,3-dioxolan-4-yl]-methane}imine was dissolved in 1 ml of anhydrous methylene chloride, and 8.7 mg (0.13 millimole, 1 eq.) of imidazole was added to the solution at room temperature. At this temperature, the reaction was carried out in an atmosphere of nitrogen for 5 minutes. The reaction solution was concentrated to dryness under reduced pressure to give 1-{[(4S)-2,2-dimethyl-1,3-dioxolan-4-yl](4-methoxy)phenylimino}methylimidazole quantitatively.

$^1$H-NMR (CDCl$_3$; δ ppm) 1.45, 1.47, 1.53, 1.60(6H, m,

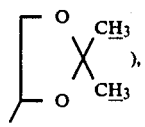

3.77, 3.86(3H, s, OC$\underline{H}_3$), 3.8–4.8(3H, m, H-4', H-5'a and H-5'b), 5.15, 5.32(1$\underline{H}$, br, Im—C$\underline{H}$—NHR), 6.40–6.95(4H, m, Ar-$\underline{H}$), 7.03(2H, m, H-4 and H-5), 7.60, 7.68(1H, s, H-2).
$\nu_{max}^{CHCl_3}$(cm$^{-1}$)=3100–3500 (NH).

EXAMPLE 2

Production of
1-{[(4S)-2,2-dimethyl-1,3-dioxolan-4-yl]-(4-methoxy)-phenylimino}methyl-1,2,4-triazole

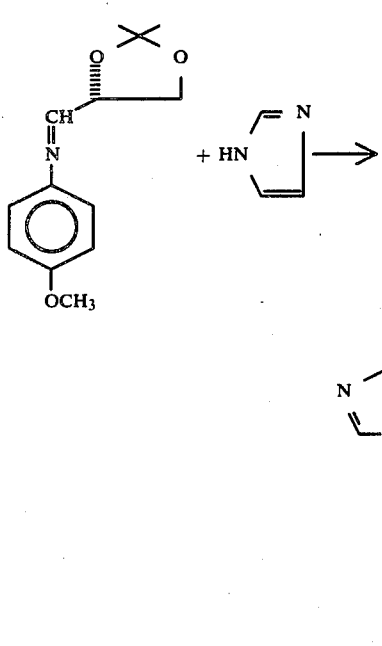

Thirty milligrams (0.13 millimole) of N-(4-methoxy)-phenyl-{[(4S)-2,2-dimethyl-1,3-dioxolan-4-yl]methane}imine was dissolved in 1 ml of anhydrous methylene chloride, and 8.97 mg (0.13 millimole) of 1,2,4-triazole was added to the solution at room temperature. At this temperature, the reaction was carried out for 10 minutes in an atmosphere of nitrogen. The reaction solution was concentrated to dryness in vacuo to give 1-{[(4S)-2,2-dimethyl-1,3-dioxolan-4-yl]-(4-methoxy)-phenylimino}methyl-1,2,4-triazole quantitatively.

$^1$H-NMR (CDCl$_3$; δ ppm): 1.68–1.87(6H, m,

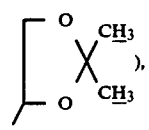

3.97, 4.04(3H, s, OC$\underline{H}_3$), 4.22–4.90(3H, m, H-4′, H-5′a and H-5′b), 5.70–5.93(1H, br,

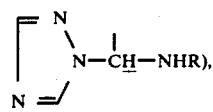

6.66–7.05(4H, m, Ar-$\underline{H}$), 8.10-(1H, s, H-3), 8.25, 8.30(1H, s, H-5).

$\nu_{max}^{CHCl_3}$(cm$^{-1}$)=3400(NH).

EXAMPLE 3

Production of
(3S,4S)-3-acetyl-4-(4S)-2,2-dimethyl-1,3-dioxolan-4-yl]-1-(4-methoxy)phenyl-2-azetidinone

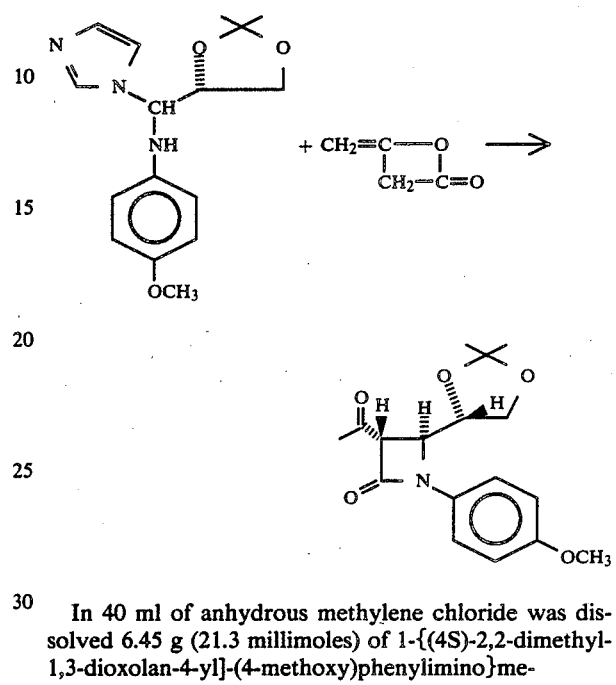

In 40 ml of anhydrous methylene chloride was dissolved 6.45 g (21.3 millimoles) of 1-{(4S)-2,2-dimethyl-1,3-dioxolan-4-yl]-(4-methoxy)phenylimino}methylimidazole, and 2.45 ml (31.95 millimoles) of diketene was added to the solution at −20° C. in an atmosphere of nitrogen. The mixture was stirred for 30 minutes at this temperature, and then for 150 minutes at room temperature. The reaction solution was poured into a mixture of methylene chloride and 0.5N hydrochloric acid containing ice and partitioned. The organic phase was separated and was washed with 0.5N hydrochloric acid (twice with 65 ml each of 0.5N hydrochloric acid). It was further washed with a saturated aqueous solution of sodium chloride, and dried over anhydrous sodium sulfate. The sodium sulfate was removed by filtration, and the filtrate was subjected to purification by silica gel column chromatography (toluene-/ethyl acetate=50/0→50/1→30/1→20/1→15/1) to give 4.60 g of the captioned compound in a yield of 67.6%.

$^1$H-NMR (CDCl$_3$; δ ppm): 1.22(3H, s,

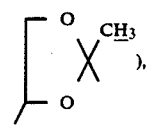

1.39(3H, s,

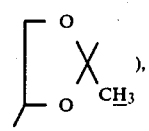

2.30(3H, s,

3.65(1H, dd, J=6.0 and 9.0 Hz, H-5'a), 3.70(3H, s, OC$\underline{H}_3$), 4.05(1H, dd, J=6.5 Hz and 9.0 Hz, H-5'b), 4.12(1H, d, J=2.5 Hz, H-3), 4.4–4.6(2H, m, H-4' and H-4), 6.75(2H, d, J=9.0 Hz, H-3" and H-5"), 7.22(2H, d, J=9.0 Hz, H-2" and H-6").

$v_{max}^{CHCl_3}$(CHCl$_3$)=1750($\beta$-lactam).

[$\alpha$]$_D^{22.5}$= –87.3° (c=1, CHCl$_3$).

EXAMPLE 4

Production of (3S,4S)-3-acetyl-4-[(4S)-2,2-dimethyl-1,3-dioxolan-4-yl]-1-(4-methoxy)phenyl-2-azetidinone

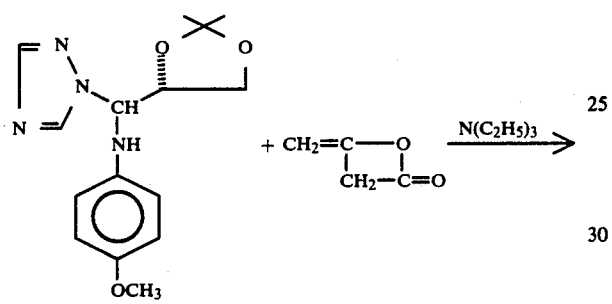

In anhydrous methylene chloride was dissolved 30 mg (0.1 millimole) of 1-{[(4S)-2,2-dimethyl-1,3-dioxolan-4-yl]-(4-methoxy)phenylimino}methyl-1,2,4-triazole obtained in Example 2, and 13.9 μl (0.1 millimole; 1 eq.) of triethylamine was added at –20° C. in an atmosphere of nitrogen. Diketene (11.5 μl, 0.15 millimoles, 1.5 eq.) was added to the solution, and the mixture was stirred at room temperature for 3 hours. The reaction solution was then poured into a mixture of methylene chloride, 0.5N hydrochloric acid and ice, and partitioned. The organic layer was separated, washed with 0.5N hydrochloric acid and successively with a saturated aqueous solution of sodium chloride, and then dried over anhydrous sodium sulfate. The filtrate was submitted to silica gel column chromatography (as described above) to give 3.1 mg of the captioned compound in a yield of 10%. Its physical and chemical properties agreed with those of the compound obtained in Example 3.

EXAMPLE 5

Production of (3S,4S)-3-(1S)-1-hydroxyethyl]-4-[(4S)-2,2-dimethyl-1,3-dioxolan-4-yl-1-(4-methoxy)phenyl-2-azetidinone

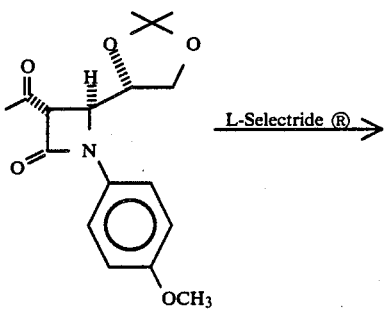

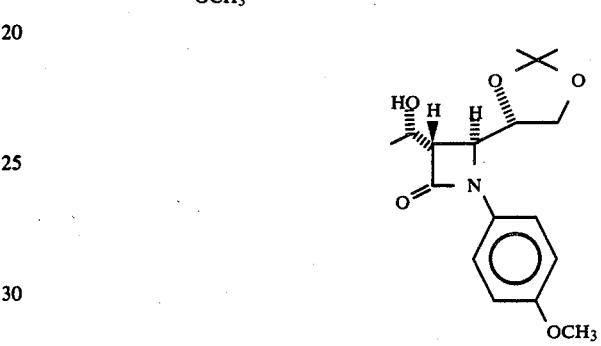

Three hundred milligams (0.94 millimole) of (3S,4S)-3-acetyl-4-[(4S)-2,2-dimethyl-1,3-dioxolan-4yl]-1-(4-methoxy)phenyl-2-azetidinone was dissolved in 5.5 ml of anhydrous tetrahydrofuran, and 1.13 ml (1.13 millimoles, 1.2 eq.) of lithium tri-sec-butylborohydride (L-selectride®) was added dropwise to the solution at –70° C. in an atmosphere of nitrogen. At this temperature, the mixture was stirred for 1 hour, and then 0.135 ml (2.37 millimoles, 2.1 eq.) of acetic acid was added. The mixture was stirred for 5 minutes, and extracted twice with 30 ml each of ethyl acetate. The extracts were combined and washed twice with 10 ml each of a saturated aqueous solution of sodium chloride, once with 15 ml of a saturated aqueous solution of sodium hydrogen carbonate and again with 10 ml of a saturated aqueous solution of sodium chloride, and dried over anhydrous sodium sulfate. The sodium sulfate was removed by filtration and the filtrate was subjected to purification by silica gel column chromatography (toluene/ethyl acetate=5/0→5/1→3/1→2/1) to give 264.0 mg (yield 87.5%) of the captioned compound. The isomer in which a (1R)-1-hydroxyethyl group was present at the 3-position was not obtained.

$^1$H-NMR(CDCl$_3$; δ ppm): 1.29–1.38(9H, m,

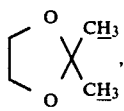

CH—C$\underline{H}_3$), 2.49(1H, d, J=3.6 Hz, OH), 3.19(1H, dd, J=2.1 and 5.1 Hz, H-3), 3.72(3H, s, OC$\underline{H}_3$), 3.62–4.20(4H, m, H-4,

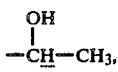

H-5′a and H-5′b), 4.45(1H, dt, J=3.5 Hz and 7.5 Hz, H-4′), 6.79(2H, d, J=9.5 Hz, H-3″ and H-5″), 7.28(2H, d, J=9.5 Hz, H-2″ and H-6″).
$\nu_{max}^{CHCl_3}$cm$^{-1}$=1739(β-lactam).
$[\alpha]_D^{23}$=−60.7°(c=1, CHCl$_3$).

EXAMPLE 6

Production of (3S,4S)-3-[(1R) and (1S)-1-hydroxyethyl-4-[(4S)-2,2-dimethyl-1,3-dioxolan-4-yl]-1-(4-methoxy)phenyl-2-azetidinone

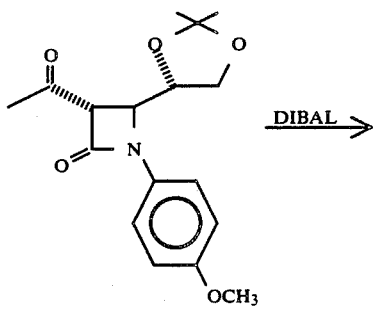

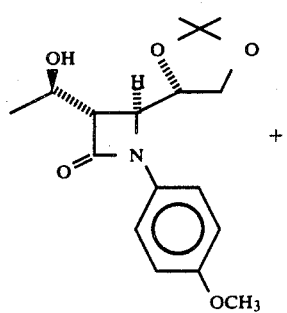

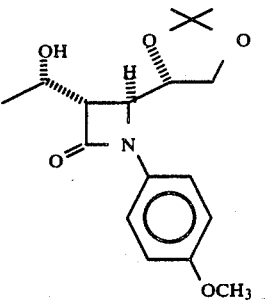

In 1.6 ml of anhydrous tetrahydrofuran was dissolved 50.3 mg (0.16 mmole) of (3S,4S)-3-acetyl-4-[(4S)-2,2-dimethyl-1,3-dioxolan-4-yl]-1-(4-methoxy)phenyl-2-azetidinone, and 240 μl (0.24 millimole, 1.5 eq.) of diisobutyl aluminum hydrate (DIBAL) was added dropwise to the solution at −70° C. in an atmosphere of nitrogen. The mixture was stirred for more than 30 minutes. After reaction, 29.3 μl (0.51 millimole) of acetic acid was added at the above temperature to stop the reaction. The reaction mixture was extracted with 20 ml of ethyl acetate. The extract was washed once each with a saturated aqueous solution of sodium chloride, a saturated aqueous solution of sodium hydrogen carbonate, and a saturated aqueous solution of sodium chloride, and then dried over anhydrous sodium sulfate. The sodium sulfate was removed by filtration, and the filtrate was subjected to silica gel column chromatography (toluene/ethyl acetate=5/0→5/1→3/1→2/1; charged with CH$_2$Cl$_2$) to give 32 mg of a mixture of (3S,4S)-3-[(1R)- and (1S)-1-hydroxy]ethyl-4-[(4S)-2,2-dimethyl-1,3-dioxolan-4-yl]-1-(4-methoxy)phenyl-2-azetidinone in a yield of 64%. The ratio of the (1R)-isomer to the (1S)-isomer in the mixture was about 3:1.
$^1$H-NMR(CDCl$_3$; δ ppm): 1.28–1.50(9H, m,

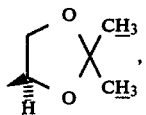

CH—CH$_3$), 2.12–2.40(1H, m, OH), 3.10(⅔H, dd, J=2.5 and 6.0 Hz, H-3 of the 1R-isomer), 3.18(⅓H, dd, J=2.5 and 6.0 Hz, H-3 of the 1S-isomer form), 3.70(3H, s, OCH$_3$), 3.71–4.60(5H, m, H-4,

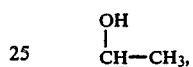

H-4′, H-5′a and H-5′b), 6.79(2H, d, J=9 Hz, H-3″ and H-5″), 7.28(2H, d, J=9 Hz, H-2″ and H-6″).

EXAMPLE 7-1

Production of (3R,4S)-3-[(1R)-1-fluoroethyl]-4-[(4S)-2,2-dimethyl-1,3-dioxolan-4-yl]-1-(4-methoxy)phenyl-2-azetidinone

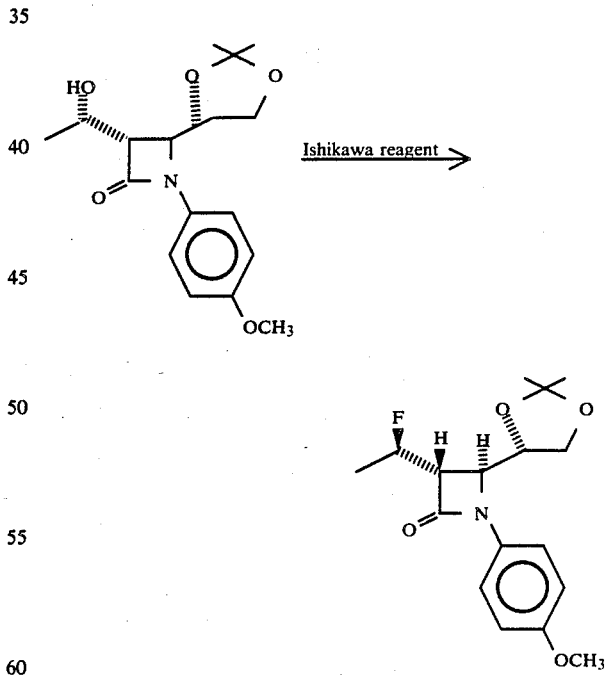

In 1.5 ml of anhydrous methylene chloride was dissolved 87.9 mg (0.27 mmole) of (3S,4S)-3-(1S)-1-hydroxyethyl]-4-[(4S)-2,2-dimethyl-1,3-dioxolan-4-yl]-(4-methoxy)phenyl-2-azetidinone, and 60.8 μl (0.18 millimole) of a mixed reagent of hexafluoropropene/diethylamine (Ishikawa reagent) was added dropwise to the solution at 0° C. in an atmosphere of nitrogen. The reaction mixture was warmed to 15° C., and stirred for 40 minutes. After reaction, 20 ml of phosphate buffer (pH 7.4; 0° C.) was added to the solution, and the mixture was stirred for 5 minutes. The reaction mixture was then extracted twice with 20 and 10 ml of methylene chloride. The organic layers were combined, washed with a saturated aqueous solution of sodium chloride, and dried over anhydrous sodium sulfate. The sodium sulfate was removed by filtration, and the filtrate was submitted to silica gel column chromatography (toluene/E-tOAc=20/0→20/1→15/1→10/1→5/1→3/1) to give 56.1 mg of the captioned compound in a yield of 64.3%.

$^1$H-NMR(CDCl$_3$; δ ppm): 1.26(3H, s,

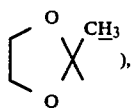

), 1.33(3H, s,

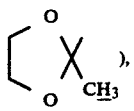

), 1.45(3H, dd, J=6 and 24 Hz, CHF-CH$_3$), 3.19(1H, ddd, J=2.4, 7.5 and 16.5 Hz, H-3), 3.62(3H, s, OCH$_3$), 3.6–4.0(3H, m, H-4, H-5a' and H-5b') 4.31 (1H, dt, J=2.4 and 6.0 Hz, H-4')4.74(1H, ddq, J=46.5, 7.5 and 6.0 Hz, CHF-CH$_3$), 6.58(2H, d, J=9 Hz, H-3" and H-5"), 7.03(2H, d, J=9Hz, H-2" and H-6").

$\nu_{max}^{CHCl_3}$cm$^{-1}$=1742(β-lactam).

[α]$_D^{22.5}$=−76.4° (c=1, CHCl$_3$).

EXAMPLE 7-2

Production of (3R,4S)-3-[(1R)-1-fluoroethyl]-4-(4S)-2,2-dimethyl-1,3-dioxolan-4-yl)-1-(4-methoxy)phenyl-2-azetidinone (an alternative method)

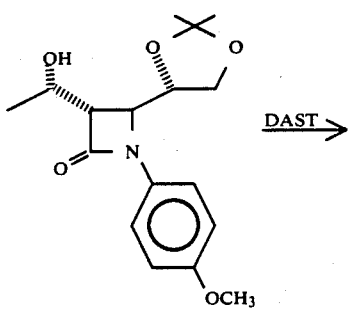

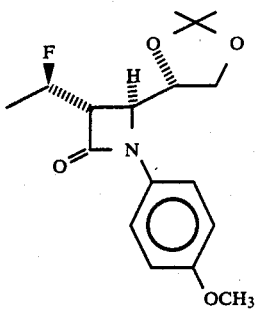

In 3 ml of anhydrous methylene chloride was dissolved 151.8 mg (0.47 millimole) of (3S,4S)-3-[(1S)-1-hydroxyethyl)-4-[(4S)-2,2-dimethyl-1,3-dioxolan-4-yl]-1-(4-methoxy)phenyl-2-azetidinone, and 93.1 μl (0.71 millimole, 1.5 eq.) of diethyl aminosulfate trifluoride (DAST) of diethylaminosulfur trifluoride (DAST) was added dropwise to the solution at −50° C. in an atmosphere of nitrogen. The mixture was stirred for 1 hour, and then poured into a mixture of a saturated aqueous solution of sodium hydrogen carbonate, methylene chloride and ice for inactivation of the excess of DAST. The organic layer was separated and washed with a saturated aqueous solution of sodium chloride. After drying over anhydrous sodium sulfate, the filtrate was subjected to silica gel column chromatography (toluene/E-tOAc=20/0→20/1→15/1→10/1→5/1→3/1) to give 71.2 mg (yield 46.9%) of the captioned compound. The physical and chemical properties of this compound agreed with those of the compound obtained in Example 7-1.

EXAMPLE 8

Production of (3R,4S)-4-[(1S)-1,2-dihydroxy ethyl)-3-[(1R)-1-fluoroethyl)-1-(4-methoxy)phenyl-2-azetidinone

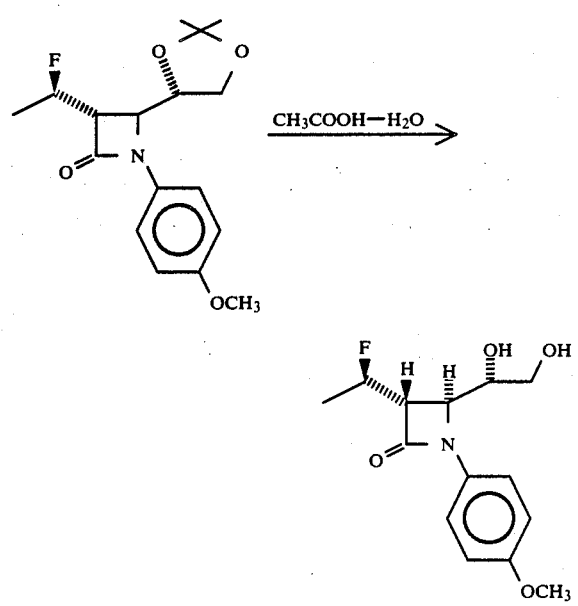

In 10.4 ml of a mixture of acetic acid and water (4:1) was dissolved 127.3 mg (0.39 millimole) of (3R,4S)-3-

(1R)-1-fluoroethyl]-4-(4S)-2,2-dimethyl-1,3-dioxolan-4-yl]-1-(4-methoxy)phenyl-2-azetidinone, and incubated at 40° C. for 14 hours. After reaction, the reaction solution was concentrated, and subjected to purification by silica gel column chromatography (toluene/EtOAc=2/0→2/1→1/1→1/2→1/3; charged with methylene chloride) to give 104.3 mg (yield 94.5%) of the captioned compound.

$^1$H-NMR(CDCl$_3$; δ ppm): 1.42(3H, dd, J=7.2 and 24.6 Hz, CHF-C$\underline{H}$$_3$), 2.85(1H, t, J=6.0 Hz, 2'-O$\underline{H}$), 3.30(1H, m, H-$\underline{3}$), 3.55(2H, m, H-5'a and H-5'b), 3.70(3H, s, OC$\underline{H}$$_3$), 4.04–4.15(2H, m, H-4 and H-4'), 4.87(1H, ddq, J=7.2 and 48.0 Hz, J=5.4 Hz, C$\underline{H}$F-CH$_3$), 6.73(2H, d, J=9.3 Hz, H-3" and H-5"), 7.20(2H, d, J=9.3 Hz, H-2" and H-6").

$\nu_{max}^{CHCl_3}$(cm$^{-1}$)=1739(β-lactam).

$[α]_D^{22}$=−63.4° (c=1.19, CHCl$_3$).

EXAMPLE 9

Production of (3R,4S)-3-[(1R)-1-fluoroethyl]-4-formyl-1-(4-methoxy)-phenyl-2-azetidinone

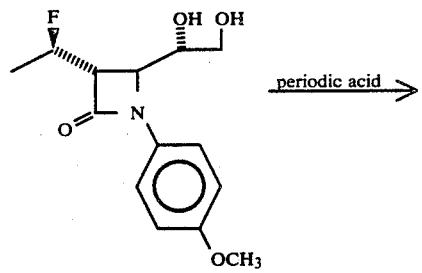

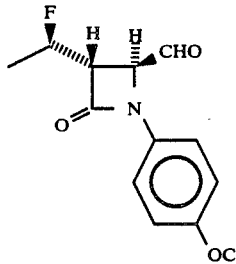

In 0.8 ml of tetrahydrofuran (THF) was dissolved 47.5 mg (0.17 millimole) of (3R,4S)-4-[(1S)-1,2-dihydroxyethyl]-3-[(1R)-1-fluoroethyl)-1-(4-methoxy)phenyl-2-azetidinone, and a solution of 48.4 mg (0.21 mmole, 1.25 eq.) of periodic acid in 1 ml of THF was added to the solution in an atmosphere of nitrogen. After reaction, the reaction solution was extracted with 30 ml of ethyl acetate. The extract was washed once each with a saturated aqueous solution of sodium hydrogen carbonate, a saturated aqueous solution of sodium sulfite and a saturated aqueous solution of sodium chloride, and then purified by silica gel column chromatography (toluene/EtOAc=3/0→3/1→2/1→1/1→1/2→1/3; charged with methylene chloride) to give 26.0 mg (yield 61.0%) of the captioned compound.

$^1$H-NMR(CDCl$_3$; δ ppm): 1.49(3H, dd, J=6.0 and 24 Hz, CHF-C$\underline{H}$$_3$), 3.35(1H, ddd, J=2.7, 5.7 and 21 Hz, H-$\underline{3}$), 3.72(3$\underline{H}$, s, OCH$_3$), 4.40(1H, dd, J=2.7 and 3.0 Hz, H-4), 5.0(1H, ddq, J=46.2, 5.7 and 6.0 Hz, C$\underline{H}$F-CH$_3$), 6.75(2H, d, J=9 Hz, H-3'and H-5'), 7.12(2$\underline{H}$, d, J=9 Hz, H-2' and H-6'), 9.65(1H, d, J=3 Hz, CHO).

$\nu_{max}^{CHCl_3}$(cm$^{-1}$)=1750(β-lactam), 1730(formyl).

$[α]_D^{22}$=−118.9°(c=1, CHCl$_3$).

EXAMPLE 10

Production of (3R,4S)-4-carboxy-3-[(1R)-1-fluoroethyl-1-(4-methoxy)phenyl-2-azetidinone

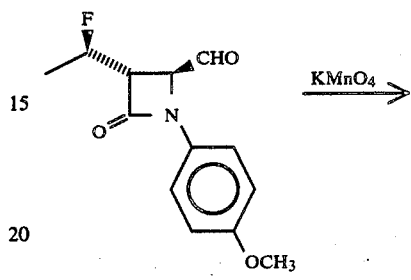

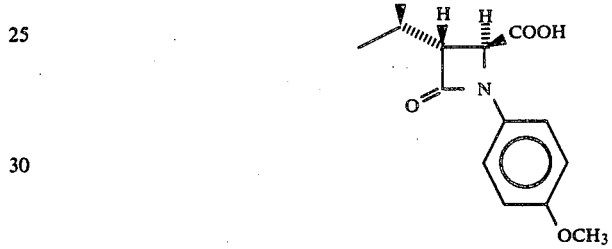

In 1 ml of butanol was dissolved 40.6 mg (0.16 mmole) of (3R,4S)-3-(1R)-1-fluoroethyl-4-formyl-1-(4-methoxy)phenyl-2-azetidinone, and 0.64 ml of phosphate buffer (pH 6.7) and 0.96 ml of 1M potassium permanganate were added to the solution. The mixture was stirred for 45 minutes. After reaction, 4 ml of a saturated aqueous solution of sodium sulfite was added and stirred under ice cooling. The mixture was then adjusted to a pH of 2 to 3 with 1N hydrochloric acid, and extracted twice with 25 ml each of ethyl acetate. The organic layers were combined and washed with a saturated aqueous solution of sodium chloride. The aqueous sodium chloride layer was re-extracted with ethyl acetate. The organic extracts were combined and dried over anhydrous sodium sulfate. The sodium sulfate was removed by filtration, and the filtrate was concentrated to dryness to give 45.6 mg of the captioned compound quantitatively.

$^1$H-NMR(CDCl$_3$; δ ppm): 1.32(3H, dd, J=6.3 and 24 Hz, CHF-C$\underline{H}$$_3$), 3.32(1H, ddd, J=3, 4.8, and 25.2 Hz, H-3), 3.58(3H, s, OC$\underline{H}$$_3$), 4.38(1H, d, J=3 Hz, H-4), 4.95(1H, ddq, J=4.8, 48 and 6.3 Hz, C$\underline{H}$F-CH$_3$), 6.73(2H, d, J=9 Hz, H-3' and H-5'), 7.08(2H, d, J=9 Hz, H-2' and H-6'), 8.72(1H, s, COO$\underline{H}$).

$\nu_{max}^{CHCl_3}$(cm$^{-1}$)=1745(β-lactam)

$[α]_D^{22}$=−84.6°(c=1.0, CH$_3$OH).

EXAMPLE 11

Production of (3R,4R)- and (3R,4S)-4-acetoxy-3-[(R)-1-fluoroethyl]-1-(p-methoxy)-phenyl-2-azetidinone

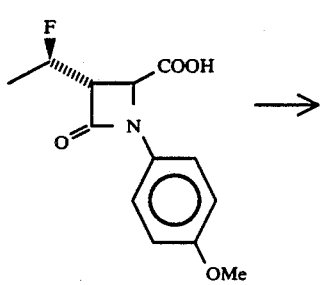

→

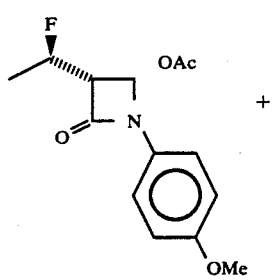

+

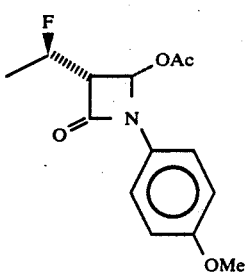

A mixture composed of 65 mg (0.24 millimole) of (3R,4S)-4-carboxy-3-(R)-1-fluoroethyl-1-(p-methoxy)-phenyl-2-azetidinone, 216 mg (0.49 millimole) of lead tetraacetate, 0.2 ml of acetic acid and 0.6 ml of dimethylformamide was reacted at 65° C. for 15 minutes. The reaction solution was poured into ethyl acetate, washed with a saturated aqueous solution of sodium chloride, and dried over anhydrous sodium sulfate. The solvent was evaporated off, and the residue was dissolved in benzene and charged on a column of silica gel (7 g). The column was eluted with benzene/ethyl acetate (50/0, 50/1, 40/1, 20/1). Eluate fractions which contained ultraviolet-absorbeing materials at Rf 0.75 and 0.57 by silica gel TLC [developed with benzene/ethyl acetate (3/1)] were collected and concentrated under reduced pressure to give 7 mg of a cis-isomer of the desired compound and 43 mg of its trans-isomer (total yield 73%). These compounds were crystallized from benzene/n-hexane.

Physical and Chemical Properties of the Cis Compound

Melting point: 156°–160° C.

$[\alpha]_D^{22} +42.7°(c=0.62, CHCl_3)$.

$\lambda_{max}^{CH2Cl2}$ nm($\epsilon$): 255(21000).

$\nu_{max}^{CHCl3}$ cm$^{-1}$: 1760($\beta$-lactam, ester CO).

$^1$H-NMR(CDCl$_3$; $\delta$ ppm): 1.60(3H, dd, J=24.0 and 6.0 Hz, C$\underline{H}_3$-CHF), 2.17(3H, s, OAc), 3.68(1H, m, H-3), 3.70(3H, s, OMe), 5.17(1H, m, CH$_3$-C$\underline{H}$F), 6.83(1H, d, J=6.0 Hz, H-4), 6.90(2H, d, J=9.0 Hz,

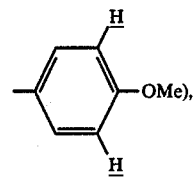

7.37(2H, d, J=9.0 Hz,

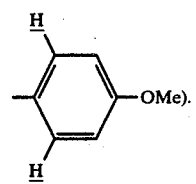

Physical and Chemical Properties of the Trans Compound

Melting point: 121°–123.5° C.

$[\alpha]_D^{22} -51.4°(c=1.013, CHCl_3)$.

$\lambda_{max}^{CH2Cl2}$ nm($\epsilon$): 254(18400).

$\nu_{max}^{CHCl3}$ cm$^{-1}$: 1760($\beta$-lactam, ester CO).

$^1$H-NMR(CDCl$_3$; $\delta$ ppm): 1.55(3H, d, J=24.0 and 6.5 Hz, C$\underline{H}_3$-CHF), 2.10(3H, s, OAc), 3.40(1H, ddd, J=1.5, 5.0 and 24.5 Hz, H-3), 3.79(3H, s, OMe), 5.07(1H, ddq, H=48.0, 5.0 and 6.5 Hz, CH$_3$-C$\underline{H}$F-), 6.62(1H, d, J=1.5 Hz, H-4), 6.90(2H, d, J=9.0 Hz,

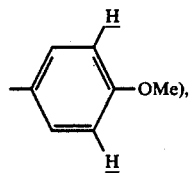

7.36(2H, d, J=9.0 Hz,

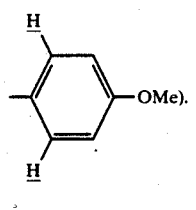

EXAMPLE 12

Production of (3R,4R)-4-acetoxy-3-[(R)-1-fluoroethyl]-2-azetidinone

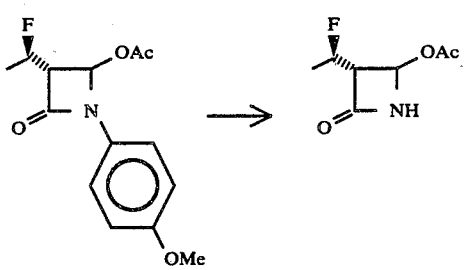

In 1.5 ml of acetonitrile was dissolved 30 mg (0.11 millimole) of (3R,4R)-4-acetoxy-3-(R)-1-fluoroethyl]-1-(p-methoxy)phenyl-2-azetidinone, and the solution was cooled with ice. Then, 1.5 ml of an aqueous solution containing 175.5 mg (0.32 millimole) of ceric ammonium nitrate was gradually dropped to the solution.

The reaction was carried out at 0° C. temperature for 25 minutes, and the reaction mixture was poured into 50 ml of ethyl acetate and washed with a 5% aqueous solution of sodium hydrogen carbonate. The aqueous wash was back extracted with ethyl cetate, and the ethyl acetate extract was combined with the organic layer. The organic solution was washed once each with a 10% aqueous solution of sodium thiosulfate, a 5% aqueous solution of sodium hydrogen carbonate and a saturated aqueous solution of sodium chloride.

The organic layer was separated and dried over anhydrous sodium sulfate, and the filtrate was concentrated under reduced pressure to give 15 mg (yield 81%) of the captioned compound.

This compound was crystallized from benzene/n-hexane.

Melting point: 98.5°–102° C.
$[\alpha]_D^{22}+116.8°(c=1.0, CHCl_3)$.
$\nu_{max}^{CHCl_3}$ cm$^{-1}$: 1780($\beta$-lactam CO),
$^1$H-NMR(CDCl$_3$; $\delta$ ppm): 1.50(3H, dd, J=6.5 and 24.0 Hz, CH$_3$-CHF), 2.13(3H, s, COCH$_3$), 3.40(1H, ddd, J=1.5, 5.5 and 24.0 Hz, H-3), 5.00(1H, dquint, J=48.0 and 6.5 Hz, CH$_3$-CHF-), 5.90(1H, d, J=1.5 Hz, H-4), 6.85(1H, br, NH).

EXAMPLE 13

Production of p-nitrobenzyl 4-[(3R,4R)-3-(R)-1-fluoroethyl)-2-oxoazetidin-4-yl-2-diazo-3-oxobutyrate

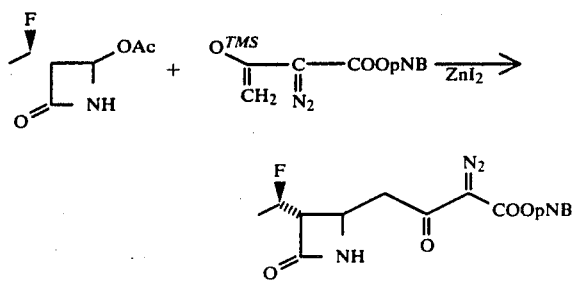

Twenty milligrams (0.11 millimole) of (3R,4R)-4-acetoxy-3-[(R)-1-fluoroethyl-2-azetidinone was dissolved in 1 ml of methylene chloride, and the solution was cooled with ice. Then, 36 mg (0.11 millimole) of zinc iodide was added to the solution. A methylene chloride solution (1 ml) containing 96 mg (0.29 millimole) of p-nitrobenzyl 2-diazo-3-(trimethylsilyl)oxy-3-butenoate was slowly dropped to the mixture over the course of 13 minutes at 0° C.

The reaction solution was stirred at 0° C. for 20 minutes and then at room temperature for 2 hours. The reaction mixture was diluted with ethyl acetate, washed successively with a 5% aqueous solution of sodium hydrogen carbonate, water, and a saturated aqueous solution of sodium chloride, and then dried over anhydrous sodium sulfate.

The solvent was evaporated off from the filtrate, and the residue was adsorbed on a 6 g silica gel column using a small amount of methylene chloride. The column was developed stepwise with benzene acetone (10/1, 8/1, 5/1). Those elutate fractions which contained a UV-absorbing material at an Rf of 0.36 on TLC developed with benzene/acetone (3/1)] were collected and concentrated to dryness under reduced pressure to give 27 mg (yield 62%) of the captioned compound.

Physical and Chemical Properties of the Resulting Compound

Melting point: 90°–92° C.
$[\alpha]_D^{22}+41.8°(c\ 1.25, methanol)$.
$\nu_{max}^{CHCl_3}$ cm$^{-1}$: 2140(diazo), 1760($\beta$-lactam CO), 1710(ketone CO), 1520, 1345(nitro).
$^1$H-NMR(CDCl$_3$; $\delta$ ppm): 1.44(3H, dd, J=24.0 and 6.5 Hz, CH$_3$—CHF—), 2.8–3.2(1H, m, H-3), 3.02(1H, dd, J=18.0 and 9.0 Hz,

3.67(1H, dd, J=18.0 and 4.5 Hz,

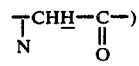

4.02(1H, ddd, J=9.0, 4.5 and 2.3 Hz, H-4), 4.93(1H, dqunit, J=48.0 and 6.5 Hz, CH$_3$CH—F—), 5.38(2H, s, benzyl), 6.30(1H, br, NH), 7.56(2H, d, J=9.0 Hz, Ar), 8.28(2H, d, J=9.0 Hz, Ar).

EXAMPLE 14

Production of (3R,4S)-4-acetoxy-3-[(R)-1-fluoroethyl-2-azetidinone

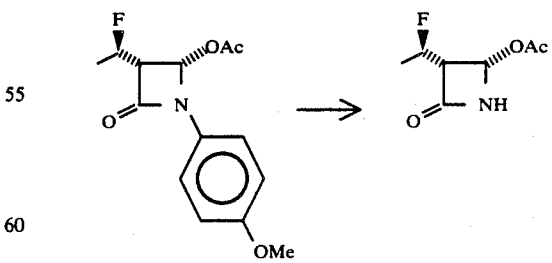

In 1.0 ml of acetonitrile was dissolved 27 mg (0.096 mmole) of (3R,4S)-4-acetoxy-3-[(R)-1-fluoroethyl)]-1-(p-methoxy)phenyl-2-azetidinone, and the solution was cooled with ice. An aqueous solution (1.0 ml) of 132 mg (0.24 millimole) of ceric ammonium nitrate was gradually added dropwise to the solution.

The solution was reacted at 0° C. for 30 minutes, and the reaction mixture was poured into ethyl acetate and washed with a 5% aqueous solution of sodium hydrogen carbonate. The aqueous layer was back-extracted with ethyl acetate. The organic layers were combined and washed successively with a 10% aqueous solution of sodium thiosulfate, a 5% aqueous solution of sodium hydrogen carbonate and a saturated aqueous solution of sodium chloride.

The washed product was dried over anhydrous sodium sulfate, and the solvent was evaporated off from the filtrate to give 15 mg (yield 89%) of the captioned compound.

$\nu_{max}^{CHCl_3}$ cm$^{-1}$: 3390(NH), 1780($\beta$-lactan CO), 1735(ester CO).

$^1$H-NMR(CDCl$_3$; $\delta$ ppm): 1.55(3H, dd, J=6.0 and 24.0 Hz, CH$_3$—CHF—), 2.17(3H, s, COCH$_3$), 3.58(1H, dddd, J$_3$, nh̄=2.0, J$_{3,4}$=4.5, J$_3$, chf=9.3, J$_3$, f=13.8 Hz, H-3), 5.13(1H, ddq, J=48.0, 9.3 and 6.0 Hz, CH$_3$CHF—), 6.02(1H, d, J=4.5 Hz, H-4), 6.80(1H, br, NH).

EXAMPLE 15

Production of p-nitrobenzyl 4-[(3R,4R)-3-[(R)-1-fluoroethyl)-2-oxoazetidin-4-yl]-2-diazo-3-oxobutyrate

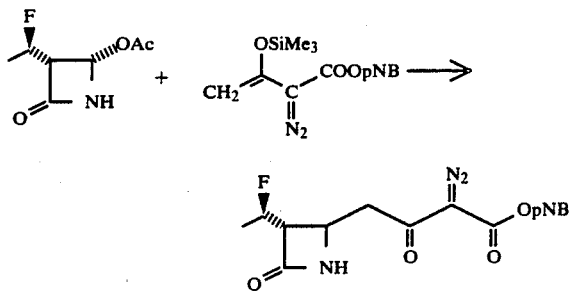

In 1 m of methylene chloride was dissolved (15 mg (0.086 millimole) of (3R,4S)-4-acetoxy-3-[(R)-fluoroethyl)-2-azetidinone, and the solution was cooled with ice. Then, 28 mg (0.087 millimole) of zinc iodide was added, and a methylene chloride solution (0.5 ml) of 72 mg (0.21 millimole) of p-nitrobenzyl 2-diazo-3-(trimethylsilyl)oxy-3-butenoate was slowly added dropwise to the mixture over the course of 10 minutes at 0° C.

The reaction solution was stirred at 0° C. for 10 minutes and then at room temperature for 2 hours. The reaction mixture was diluted with ethyl acetate, and successively washed with a 5% aqueous solution of sodium hydrogen carbonate, water and a saturated aqueous solution of sodium chloride. The organic solution was dried over anhydrous sodium sulfate, and the solvent was removed from the filtrate by evaporation. The residue was purified by preparative TLC developing system=benzene/acetone (3/1)) to give 13.7 mg (yield 42%) of the captioned compound.

The physical and chemical properties of the resulting compound completely agreed with those of the compound obtained in Example 13.

INDUSTRIAL APPLICABILITY

The compounds of formula (I) provided by this invention are useful as synthesis intermediates for various medicines, particularly carbapenam or carbapenem antibiotics, for example an antibiotic of the following formula which is known to have excellent antimicrobial activity and relatively good stability to kidney dehydropeptidase.

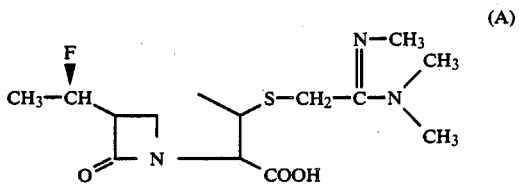

We claim:
1. A compound represented by the formula

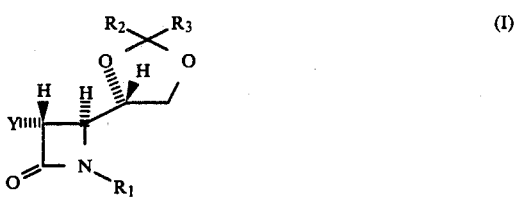

wherein Y represents an acetyl, 1-hydroxyethyl or 1-fluoroethyl group, R$_1$ represents a hydrogen atom or a tri(lower alkyl) silyl group, a benzyl group which may be substituted by one or two lower alkoxy groups, or a phenyl group which may be substituted by one or two lower alkoxy groups, and R$_2$ and R$_3$ are identical or different and each represents a hydrogen atom, a lower alkyl group, a phenyl group, a benzyl group or a diphenylmethyl group, or R$_2$ and R$_3$ together represent a lower alkylene group.

2. The compound of claim 1 wherein R$_1$ represents a phenyl or benzyl group which may be substituted by one or two lower alkoxy groups, or a lower alkylsilyl group.

3. The compound of claim 1 or 2 wherein R$_2$ and R$_3$ are identical or different and each represents a hydrogen atom or a lower alkyl group.

4. The compound of claim 1 which is (3S,4S)-3-acetyl-4-[(4S)-2,2-dimethyl-1,3-dioxolan-4-yl]-1-(4-methoxy)phenyl-2-azetidinone.

5. The compound of claim 1 which is (3S,4S)-4-[(4S)-2,2-dimethyl-1,3-dioxolan-4-yl]-3-[(1S)-1-hydroxyethyl-1-(4-methoxy)phenyl-2-azetidinone.

6. The compound of claim 1 which is (3R,4S)-4-[(4S)-2,2-dimethyl-1,3-dioxolan-4-yl]-3-[(1R)-1-fluoroethyl]-1-(4-methoxy)-phenyl-2-azetidinone.

7. The compound of claim 1 which is (3R,4S)-1-benzyl-4-[(4S)-2,2-dimethyl-1,3-dioxolan-4-yl-3-[(1R)-1-fluoroethyl]-azetidinone.

8. The compound of claim 1 which is (3R,4S)-1-(2,4-dimethoxy)phenyl-4-{(2S)-1,4-dioxospiro[4,5]deca-2-yl}-3-[(1R)-1-fluoroethyl]-2-azetidinone.

9. The compound of claim 1 which is (3R,4S)-4-[(4S)-2-ethyl-2-methyl-1,3-dioxolan-4-yl]-3-[(1R)-1-fluoroethyl]-1-(4-methoxy)benzyl-2-azetidinone.

10. The compound of claim 1 which is (3R,4S)-1-t-butyldimethylsilyl-3-[(1R)-1-fluoroethyl]-4-[(4S)-2-methyl-1,3-dioxolan-4-yl]-2-azetidinone.

* * * * *